US012685989B2

(12) United States Patent (10) Patent No.: US 12,685,989 B2

Yokoyama et al. (45) Date of Patent: Jul. 21, 2026

(54) TEMPERATURE UNIFORMIZED HEAT-EXCHANGE-TYPE CATALYST REACTOR

(71) Applicant: MITSUBISHI HEAVY INDUSTRIES, LTD., Tokyo (JP)

(72) Inventors: Koichi Yokoyama, Tokyo (JP); Masashi Kiyosawa, Tokyo (JP); Shuji Tanigawa, Tokyo (JP)

(73) Assignee: MITSUBISHI HEAVY INDUSTRIES, LTD., Tokyo (JP)

(*) Notice: Subject to any disclaimer, the term of this patent is extended or adjusted under 35 U.S.C. 154(b) by 497 days.

(21) Appl. No.: 18/550,138

(22) PCT Filed: Mar. 28, 2022

(86) PCT No.: PCT/JP2022/014811

§ 371 (c)(1),
(2) Date: Sep. 12, 2023

(87) PCT Pub. No.: WO2022/210469

PCT Pub. Date: Oct. 6, 2022

(65) Prior Publication Data

US 2024/0165576 A1 May 23, 2024

(30) Foreign Application Priority Data

Mar. 31, 2021 (JP) ................................ 2021-061906

(51) Int. Cl.
| | |
|---|---|
| *B01J 35/30* | (2024.01) |
| *B01J 19/00* | (2006.01) |
| *B01J 19/24* | (2006.01) |
| *C07C 1/12* | (2006.01) |
| *C07C 2/12* | (2006.01) |
| *C07C 29/152* | (2006.01) |

(52) U.S. Cl.
CPC ....... *B01J 19/2425* (2013.01); *B01J 19/0013* (2013.01); *C07C 1/12* (2013.01); *C07C 29/152* (2013.01); *B01J 35/30* (2024.01); *B01J 2219/00099* (2013.01)

(58) Field of Classification Search
CPC .... B01J 19/2425; B01J 19/0013; B01J 35/30; C07C 2/12; C07C 29/152
See application file for complete search history.

(56) References Cited

U.S. PATENT DOCUMENTS

| | | | |
|---|---|---|---|
| 3,147,084 A | 9/1964 | Franzen et al. | |
| 4,203,906 A | 5/1980 | Takada et al. | |
| 4,256,783 A | 3/1981 | Takada et al. | |

| | | | |
|---|---|---|---|
| 7,238,836 B2 * | 7/2007 | Ha | ......................... C07C 51/252 562/545 |
| 2004/0076562 A1 | 4/2004 | Manzanec et al. | |
| 2004/0234432 A1 | 11/2004 | Lomax, Jr. | |
| 2005/0049435 A1 | 3/2005 | Ha et al. | |
| 2013/0032762 A1 | 2/2013 | Quintero et al. | |
| 2016/0145114 A1 | 5/2016 | Glockler et al. | |

FOREIGN PATENT DOCUMENTS

| | | |
|---|---|---|
| GB | 2372462 A | 8/2002 |
| JP | S54-19480 A | 2/1979 |
| JP | H05-186203 A | 7/1993 |
| JP | 2002-143675 A | 5/2002 |
| JP | 2005-177624 A | 7/2005 |
| JP | 2006-198533 A | 8/2006 |
| JP | 2007-503570 A | 2/2007 |
| JP | 2007-533605 A | 11/2007 |
| JP | 2007-329132 A | 12/2007 |
| JP | 2016-526523 A | 9/2016 |
| JP | 2017-209632 A | 11/2017 |
| JP | 2019-5907 A | 1/2019 |
| JP | 2020-124665 A | 8/2020 |
| WO | 2004/037418 A2 | 5/2004 |
| WO | 2011/083332 A1 | 7/2011 |

OTHER PUBLICATIONS

Office Action dated Aug. 13, 2024, issued in counterpart JP Application No. 2021-061906, with English translation. (7 pages).

English Translation of International Search Report dated Jun. 7, 2022, issued in counterpart application No. PCT/JP2022/014811. (3 pages).

Extended (supplementary) European Search Report dated Mar. 6, 2025, issued in counterpart EP Application No. 22780680.9. (8 pages).

\* cited by examiner

*Primary Examiner* — Sikarl A Witherspoon

(74) *Attorney, Agent, or Firm* — WHDA, LLP

(57) ABSTRACT

A catalyst reactor device is provided with a reactor. The reactor includes: a reaction tube including a multilayer-structure tube which is formed from a cylindrical nonporous layer and a cylindrical porous layer layered on the inner side of the nonporous layer, has a fluid inflow port and a fluid outflow port, has a reaction tube lumen contiguous from the fluid inflow port through to the fluid outflow port, and has a distribution in the thickness of the porous layer in the range from the fluid inflow port side to the fluid outflow port side, and including a catalyst carried on the porous layer; and a heating medium tube which has a heating medium inflow port and a heating medium outflow port and has a heating medium tube lumen contiguous from the heating medium inflow port through to the heating medium outflow port.

10 Claims, 6 Drawing Sheets

TEMPERATURE UNIFORMIZED HEAT-EXCHANGE-TYPE CATALYST REACTOR

TECHNICAL FIELD

The present invention relates to a catalytic reaction device. More specifically, the present invention relates to a tube-type catalytic reaction device that is excellent in removing reaction heat such that an excessive temperature difference does not occur in a longitudinal direction.

BACKGROUND ART

Various catalytic reaction devices for obtaining fluid products have been proposed.

For example, PTL 1 discloses a contact gas phase reaction method in which a columnar catalyst for contact gas phase reaction that is filled in a reaction tube for use, has a columnar shape, has a length in a longitudinal direction larger than an inner diameter of the reaction tube, and has at least one through-hole in the longitudinal direction is installed in an inlet end portion of a catalyst layer in the reaction tube and then a granular catalyst having a shape different from that of the catalyst is filled around and/or behind the catalyst for reaction.

PTL 2 discloses a catalytic reactor for gas phase reaction that has a cylindrical molded catalytic reaction tube provided therein. In the cylindrical molded catalytic reaction tube, a gradient of catalytic activity is provided in a direction from an inlet for a raw material gas to an outlet of the catalytic reactor.

PTL 3 discloses a hybrid porous tube body in which a porous alloy sprayed film is provided inside and a porous ceramic sprayed film is laminated thereon.

PTL 4 discloses a honeycomb monolithic modification catalyst which produces hydrogen-containing modified gas using hydrocarbons, molecular oxygen, and water as raw materials and in which a void ratio increases from a raw material inlet to a modified gas outlet of the catalyst.

PTL 5 discloses a diesel exhaust gas treatment device that has a molded body obtained by laminating basic units, each of which is a pair of a porous corrugated plate and a porous flat plate on which an exhaust gas purification catalyst is supported, such that corrugated plate ridge lines of the porous corrugated plates are alternately orthogonal to each other. A side surface of the molded body which is orthogonal to the corrugated plate ridge line is closed, and an exhaust gas inflow path and an exhaust gas outflow path are formed between the porous corrugated plates through the porous flat plate. The void ratio of the porous corrugated plate is smaller than the void ratio of the porous flat plate.

PTL 6 discloses a method that reacts one or more reactants in a microchannel in the presence of a stepwise catalyst to form one or more products. Here, the stepwise catalyst has a distribution of a catalytically active material such that, in some regions of the catalyst, one or more reactants are exposed to a higher concentration of catalytically active material than in other regions of the catalyst.

CITATION LIST

Patent Literature

[PTL 1] Japanese Unexamined Patent Application Publication No. 2017-209632

[PTL 2] Japanese Unexamined Patent Application Publication No. 2020-124665

[PTL 3] Japanese Unexamined Patent Application Publication No. 2007-329132

[PTL 4] Japanese Unexamined Patent Application Publication No. 2005-177624

[PTL 5] Japanese Unexamined Patent Application Publication No. 2006-198533

[PTL 6] WO2004/37418 A

SUMMARY OF INVENTION

Technical Problem

An object of the present invention is to provide a tube-type catalytic reaction device that is excellent in removing reaction heat such that an excessive temperature difference does not occur in a longitudinal direction.

Solution to Problem

In order to achieve the object, the present invention including the following aspects has been completed.

[1] There is provided a reaction tube including: a multi-layer structure tube that is composed of a tubular non-porous layer and a tubular porous layer laminated inside the tubular non-porous layer, has a fluid inlet, a fluid outlet, and a reaction tube inner cavity communicating from the fluid inlet to the fluid outlet, and has a distribution in a thickness of the porous layer in a range from the fluid inlet to the fluid outlet; and a catalyst that is supported on the porous layer.

[2] In the reaction tube according to [1], the thickness of the porous layer may be larger on a fluid outlet side than on a fluid inlet side or may be larger on the fluid inlet side than on the fluid outlet side.

[3] In the reaction tube according to [1] or [2], a sum of the thickness of the porous layer and a thickness of the non-porous layer may be substantially constant in the range from the fluid inlet to the fluid outlet.

[4] There is provided a reaction tube including two or more short reaction tubes. Each of the short reaction tubes includes a multilayer structure tube that is composed of a tubular non-porous layer and a tubular porous layer laminated inside the tubular non-porous layer, has a fluid inlet, a fluid outlet, and a short reaction tube inner cavity communicating from the fluid inlet to the fluid outlet and a catalyst that is supported on the porous layer. The fluid outlet of one short reaction tube is connected in series to the fluid inlet of another short reaction tube such that the short reaction tube inner cavities communicate with each other, and a thickness of the porous layer of the one short reaction tube is substantially different from a thickness of the porous layer of another short reaction tube.

[5] The reaction tube according to any one of [1] to [4] may further include a plate-shaped porous layer that is provided to protrude from an inner surface of the tubular porous layer toward the reaction tube inner cavity (or the short reaction tube inner cavity).

[6] There is provided a catalytic reaction device including a reactor. The reactor includes the reaction tube according to any one of [1] to [5] and a heat transfer medium tube that has a heat transfer medium inlet, a heat transfer medium outlet, and a heat transfer medium tube inner cavity communicating from the heat transfer medium inlet to the heat transfer medium outlet. The reactor has a mechanism in which a fluid raw material flows into the reaction tube inner cavity through the fluid inlet, the fluid raw material is brought into contact with the catalyst and chemically reacts with the catalyst in the reaction tube inner cavity, and a fluid mixture including a fluid product obtained by the chemical reaction flows out from the reaction tube inner cavity through the fluid outlet, a mechanism in which the heat transfer medium flows into the heat transfer medium tube inner cavity through the heat transfer medium inlet and the heat transfer medium flows out from a first heat transfer medium tube inner cavity through the heat transfer medium outlet, and a mechanism in which the reaction tube is inserted into the heat transfer medium tube inner cavity and the heat transfer medium in the heat transfer medium tube inner cavity exchanges heat with the fluid material in the reaction tube inner cavity through a reaction tube wall.

[7] In the catalytic reaction device according to [6], there may be a plurality of the reaction tubes each of which has a plate fin provided to protrude outward from an outer surface of the multilayer structure tube, and each of the reaction tubes may be disposed parallel to a longitudinal direction of the heat transfer medium tube and may be connected to another adjacent reaction tube through the plate fin.

[8] There is provided a method for obtaining a fluid product. The method includes: supplying the fluid raw material into the reaction tube inner cavity through the fluid inlet in the catalytic reaction device according to [6] or [7]; performing a chemical reaction while controlling a temperature of the fluid material in the reaction tube inner cavity by supplying the heat transfer medium into the heat transfer medium tube inner cavity through the heat transfer medium inlet, flowing the heat transfer medium through the heat transfer medium tube inner cavity, and discharging the heat transfer medium from the heat transfer medium tube inner cavity through the heat transfer medium outlet; and discharging a fluid mixture including a fluid product obtained by the chemical reaction from the reaction tube inner cavity through the fluid outlet.

[9] In the method according to [8], the fluid raw material may include hydrogen and carbon dioxide, and the fluid product may include carbon monoxide, methanol, or methane.

[10] There is provided a method for manufacturing the reaction tube according to any one of [1] to [5]. The method includes: obtaining a multilayer structure tube that is composed of a tubular non-porous layer and a tubular porous layer laminated inside the tubular non-porous layer and that has a fluid inlet, a fluid outlet, and a reaction tube inner cavity communicating from the fluid inlet to the fluid outlet by repeatedly performing formation of a multilayer structure plate which is composed of an annular non-porous layer and an annular porous layer laminated inside the annular non-porous layer, the formation of the multilayer structure plate being performed by irradiating a spread material powder with a laser or an electron beam such that a portion corresponding to a non-porous layer is irradiated with a higher-energy laser or electron beam than a portion corresponding to a porous layer and by sintering the spread material powder; and supporting a catalyst on the porous layer.

Advantageous Effects of Invention

In a reaction tube filled with a granular catalyst, the granular catalyst has a lower thermal conductivity than a tube wall, and the heat transfer efficiency of the granular catalyst that is located at a position away from the tube wall is low. In addition, it is not easy to fill a tube having a small inner diameter with the granular catalyst.

On the other hand, the reaction tube according to the present invention is excellent in heat removal because reaction heat can be directly transferred to the non-porous layer laminated on the porous layer having the catalyst supported thereon, and an excessive temperature difference (hot spot) does not occur in the longitudinal direction. In addition, a temperature distribution caused by a chemical reaction is estimated from the relationship between a chemical reaction speed and a space velocity of a target, and the thickness of the porous layer in a portion that is likely to reach a high temperature in the estimated temperature distribution is reduced to reduce the amount of catalyst supported on the portion and to suppress a reaction rate in the portion. As a result, it is possible to prevent the occurrence of problems such as catalyst deterioration at the hot spot.

According to the method for manufacturing the reaction tube according to the present invention, even in a tube having a small inner diameter, which is difficult to fill with, for example, a granular catalyst, it is possible to easily and uniformly support the amount of catalyst necessary and sufficient for chemical reactions. According to the method for manufacturing the reaction tube according to the present invention, it is possible to ensure sufficient pressure resistance even when the thickness and weight of the tube wall are reduced in order to enhance heat transfer.

In the catalytic reaction device and the catalytic reaction method according to the present invention, the temperature distribution in the reaction tube can be uniformly controlled within a predetermined range, and a fluid product can be obtained by stably chemically reacting a fluid raw material under a desired pressure in the presence of a catalyst over a long period of time.

The present invention can be preferably used in, for example, a chemical reaction that generates methane gas and water using $CO_2$.

DESCRIPTION OF EMBODIMENTS

Figure 1:
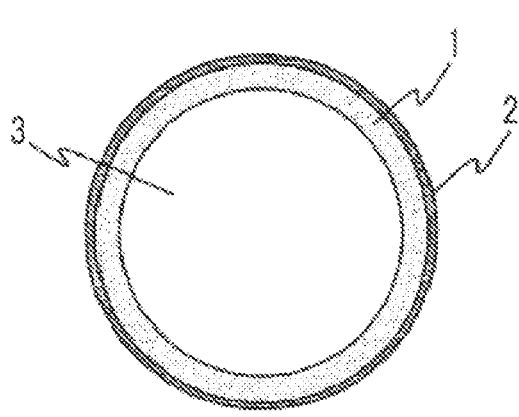
FIG. 1 is a cross-sectional view showing an example of a reaction tube according to the present invention.
Figure 2:
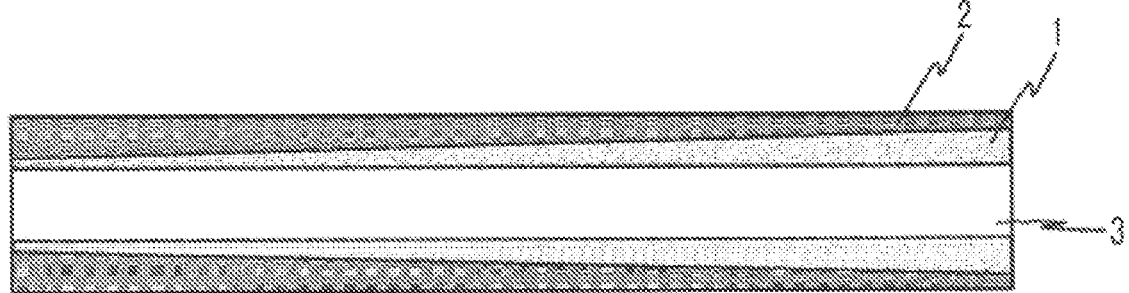
FIG. 2 is a longitudinal sectional view showing the reaction tube shown in FIG. 1.
Figure 3:
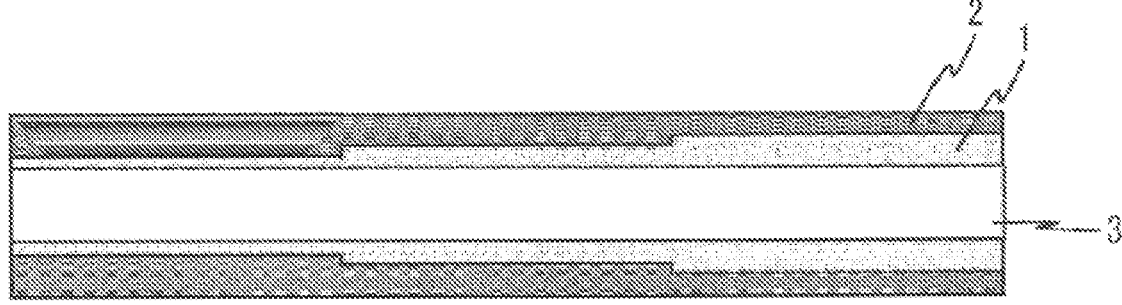
FIG. 3 is a longitudinal sectional view showing another example of the reaction tube according to the present invention.

The present invention will be described with reference to the drawings. However, the present invention is not limited to the aspects shown in the drawings.

A reaction tube according to the present invention includes a multilayer structure tube and a catalyst.

The multilayer structure tube is composed of a tubular non-porous layer 2 and a tubular porous layer 1 that is laminated inside the tubular non-porous layer 2. The multilayer structure tube has a fluid inlet and a fluid outlet and has a reaction tube inner cavity 3 that communicates from the fluid inlet to the fluid outlet. A surface (cross section) that is cut at a right angle to a longitudinal direction of the multilayer structure tube can have, for example, a circular shape, an egg shape, an elliptical shape, an oval shape, a rounded quadrangular shape, and a quadrangular shape. From the viewpoint of pressure resistance and weight reduction, it is preferable that the surface has a circular shape (see, for example, FIG. 1). An inner diameter and an outer diameter of the multilayer structure tube can be appropriately designed according to, for example, a reaction scale, strength, and withstanding pressure. In addition, when the area of a portion where the fluid flows is A and the length of the circumference (immersion side length) where the fluid is in contact with a pipeline is L in the cross section orthogonal to the longitudinal direction, the inner diameter and the outer diameter are values (equivalent diameters) defined by 4A/L. In addition, the fluid is a liquid, a gas, or a gas-liquid mixture and is preferably a gas.

The porous layer is a layer having a structure in which a large number of pores are formed. It is preferable that the porous layer has pores (communication holes) through which the fluid can pass from one end to the other end. Not all of the pores in the porous layer need to be the communication holes, and the pores may be dead-end pores as long as they have a pore volume in which the fluid can enter. Since the porous layer is a portion that serves as a carrier of the catalyst, it can be appropriately selected from, for example, a porous layer made of metal and a porous layer made of ceramics, according to a chemical reaction to be performed in the reaction tube. From the viewpoint of thermal conductivity, the porous layer is preferably made of metal.

A thickness of the porous layer is distributed in a range from the fluid inlet to the fluid outlet. For the distribution of the thickness, for example, it is preferable to estimate a temperature distribution caused by a chemical reaction from the relationship between a chemical reaction speed and a space velocity of a target and to reduce the thickness of the porous layer in a portion that is likely to reach a high temperature in the estimated temperature distribution. More specifically, in a reaction in which the temperature on the fluid outlet side is more likely to be higher than that on the fluid inlet side, the thickness is distributed such that the thickness on the fluid inlet side is larger than that on the fluid outlet side. On the contrary, in a reaction in which the temperature on the fluid inlet side is more likely to be higher than that on the fluid outlet side, the thickness is distributed such that the thickness on the fluid outlet side is larger than that on the fluid inlet side. The distribution of the thickness of the porous layer may be changed continuously or may be changed stepwise. The range of the thickness of the porous layer is not particularly limited and is, for example, from 0.1 to 2.0 mm.

For example, the relative density, void ratio, open porosity, effective porosity, and pore diameter distribution of the porous layer can be appropriately set according to the chemical reaction performed in the reaction tube. For example, the relative density of the porous layer is preferably 20% to 80%. In addition, the relative density (density index) is defined by the following equation.

$$\text{Relative density } [\%] = \text{apparent density/true density} \times 100$$

Further, the true density is a density in a case in which only the volume occupied by a solid is considered as a volume for density calculation. The density of a metal bulk can be used as the true density or the true density can be calculated on the basis of a pycnometer method. The apparent density is a density in a case in which a solid and an internal void are considered as a volume and can be calculated on the basis of the Archimedes method. The bulk density is a density in a case in which a solid, a pore, and an internal void are considered as a volume and can be calculated on the basis of a dimensioning method using, for example, a vernier caliper or a micrometer.

The non-porous layer is a layer having a dense or compact structure that does not substantially have the communication holes. The non-porous layer substantially blocks the fluid and prevents the fluid from leaking. The non-porous layer may have voids (internal voids) enclosed therein as long as the effects of the present invention can be obtained. For example, the relative density of the non-porous layer is preferably equal to or higher than 99% and most preferably 100%. The non-porous layer can be appropriately selected from, for example, a non-porous layer made of metal and a non-porous layer made of ceramics. From the viewpoint of thermal conductivity, the non-porous layer is preferably made of metal.

The range of the thickness of the non-porous layer is not particularly limited and is, for example, from 0.1 to 2.0 mm. The thickness of the non-porous layer may be distributed. For example, the sum of the thickness of the porous layer and the thickness of the non-porous layer can be substantially constant in the range from the fluid inlet to the fluid outlet.

In addition, from the viewpoint of, for example, thermal expansion, it is preferable that the porous layer and the non-porous layer are made of the same material.

The ratio of the pores from the porous layer to the non-porous layer may be changed stepwise or gradationally. In addition, the ratio of the thickness of the porous layer to the thickness of the non-porous layer is preferably 1/50 to 50/1, more preferably 1/30 to 10/1, and even more preferably 1/10 to 2/1.

The catalyst is supported on the porous layer. The catalyst can be appropriately selected according to the chemical reaction performed in the reaction tube. For example, a Ni-based catalyst, a platinum group metal-based catalyst, other noble metal-based catalysts, and the like can be used in a methanation reaction (methation) of carbon dioxide or carbon monoxide. Specific examples of the methanation catalyst can include nickel aluminate ($NiAl_xO_y$), $Ru/NiAl_xO_y$, $Ru/Al_2O_3$, $Ru/TIO_2$, $Ni/TIO_2$, and $Ru$—$Ni/TIO_2$. Specific examples of the CO selective oxidation catalyst can include $Ru/Al_2O_3$, $Ru/C$, Rh porphyrin/C, $Co_x$—$Fe_2O$, $Co_3O_4$, $Cu/CeO_2$—$ZrO_2$, $Ni/CeO_2$—$ZrO_2$, $Co/CeO_2$—$ZrO_2$, $Fe/CeO_2$—$ZrO_2$, $Pt/Al_2O_3$, $CuMn_2O_4$, CuZnO, $Pt/SiO_2$, $Pd/Al_2O_3$, $Pt/SnO_2$, $Pd/CeO_2$, $Pt/TIO_2$, $PdCl_2$—$CuCl_2/C$, $Au/TiO_2$, and $Au/Fe_2O_3$.

A method for supporting the catalyst on the porous layer is not particularly limited. For example, the catalyst can be supported by bringing an aqueous solution or dispersion liquid of a component (catalyst component) constituting the catalyst into contact with the porous layer. The aqueous solution or dispersion liquid of the catalyst component can be brought into contact with the porous layer by, for example, a method that immerses the reaction tube having the porous layer in the aqueous solution or dispersion liquid of the catalyst component or a method that makes the aqueous solution or dispersion liquid of the catalyst component flow to the reaction tube having the porous layer. After the contact, heat treatment (for example, drying or sintering) can be performed, if necessary.

Figure 4:
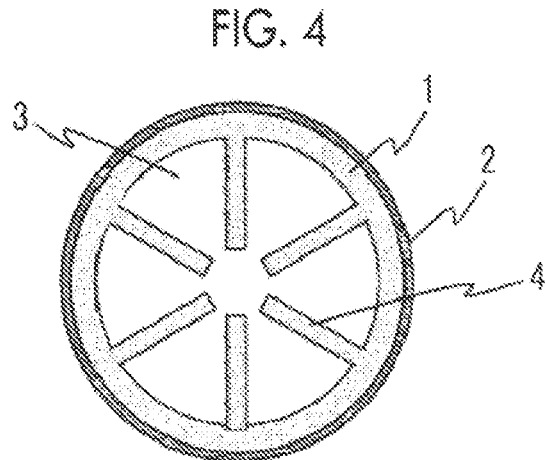
FIG. 4 is a cross-sectional view showing another example of the reaction tube according to the present invention.
Figure 5:
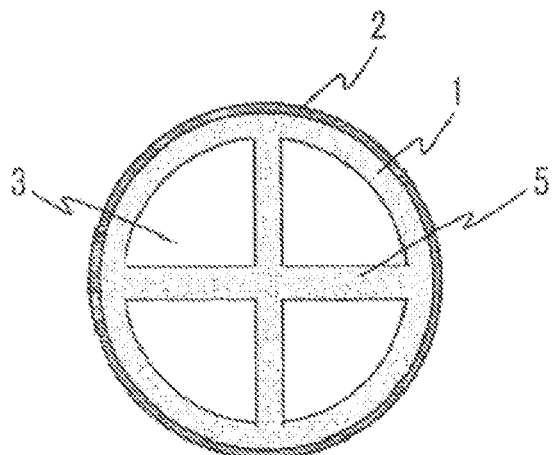
FIG. 5 is a cross-sectional view showing still another example of the reaction tube according to the present invention.
Figure 6:
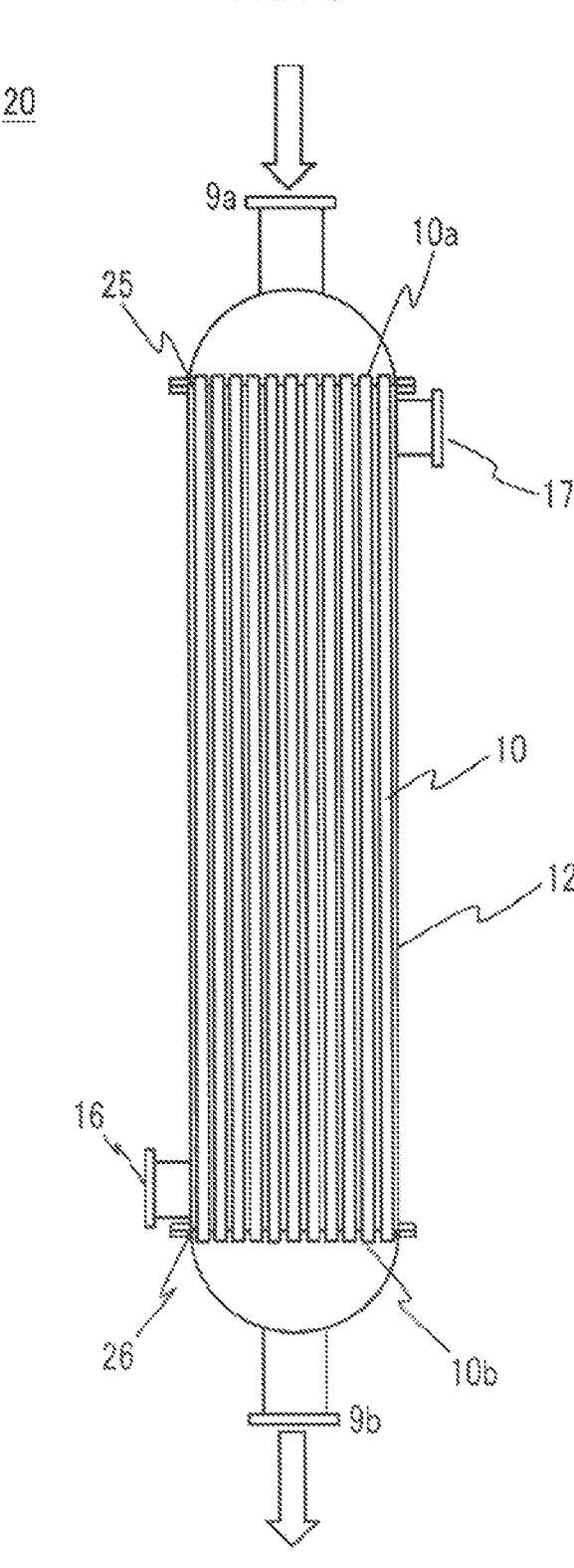
FIG. 6 is a longitudinal sectional view showing an example of a reactor according to the present invention.
Figure 7:
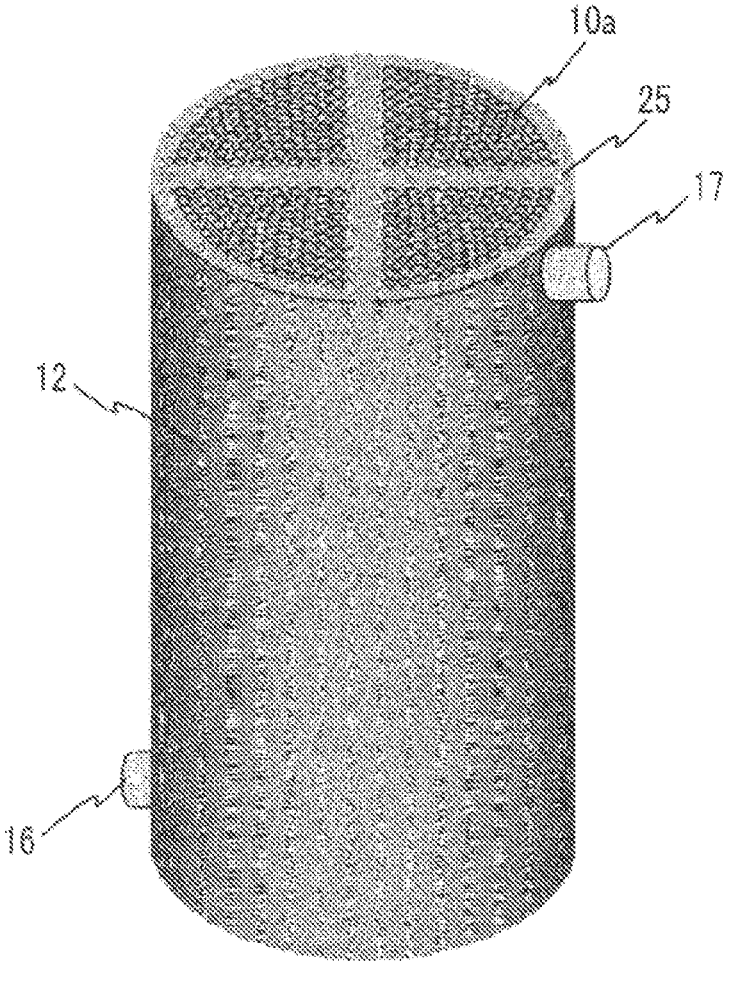
FIG. 7 is a perspective view showing an example of the appearance of the inside (a state in which an end plate is removed) of the reactor according to the present invention.

Another aspect of the reaction tube according to the present invention further includes a plate-shaped porous layer 4 that is provided to protrude from the inner surface of the tubular porous layer toward the reaction tube inner cavity (for example, FIG. 4). The shape of the plate-shaped porous layer is not particularly limited. For example, in still another aspect of the reaction tube according to the present invention, a plate-shaped porous layer 5 has a cross shape (for example, FIG. 5). In yet another aspect of the reaction tube according to the present invention, a plate-shaped porous layer has a spiral shape. The plate-shaped porous layer contributes to, for example, the control of the flow of the fluid, an increase in the amount of catalyst supported, and an increase in the contact area between the fluid and the porous layer.

Still yet another aspect of the reaction tube according to the present invention further includes a plate fin 11 that is provided to protrude outward from an outer surface of the multilayer structure tube. The plate fin may be provided such that a plate surface is parallel to the longitudinal direction of the multilayer structure tube, may be provided such that the plate surface has a spiral shape, or may be provided such that the plate surface is not parallel (for example, is at a right angle) to the longitudinal direction of the multilayer structure tube.

Figure 8:
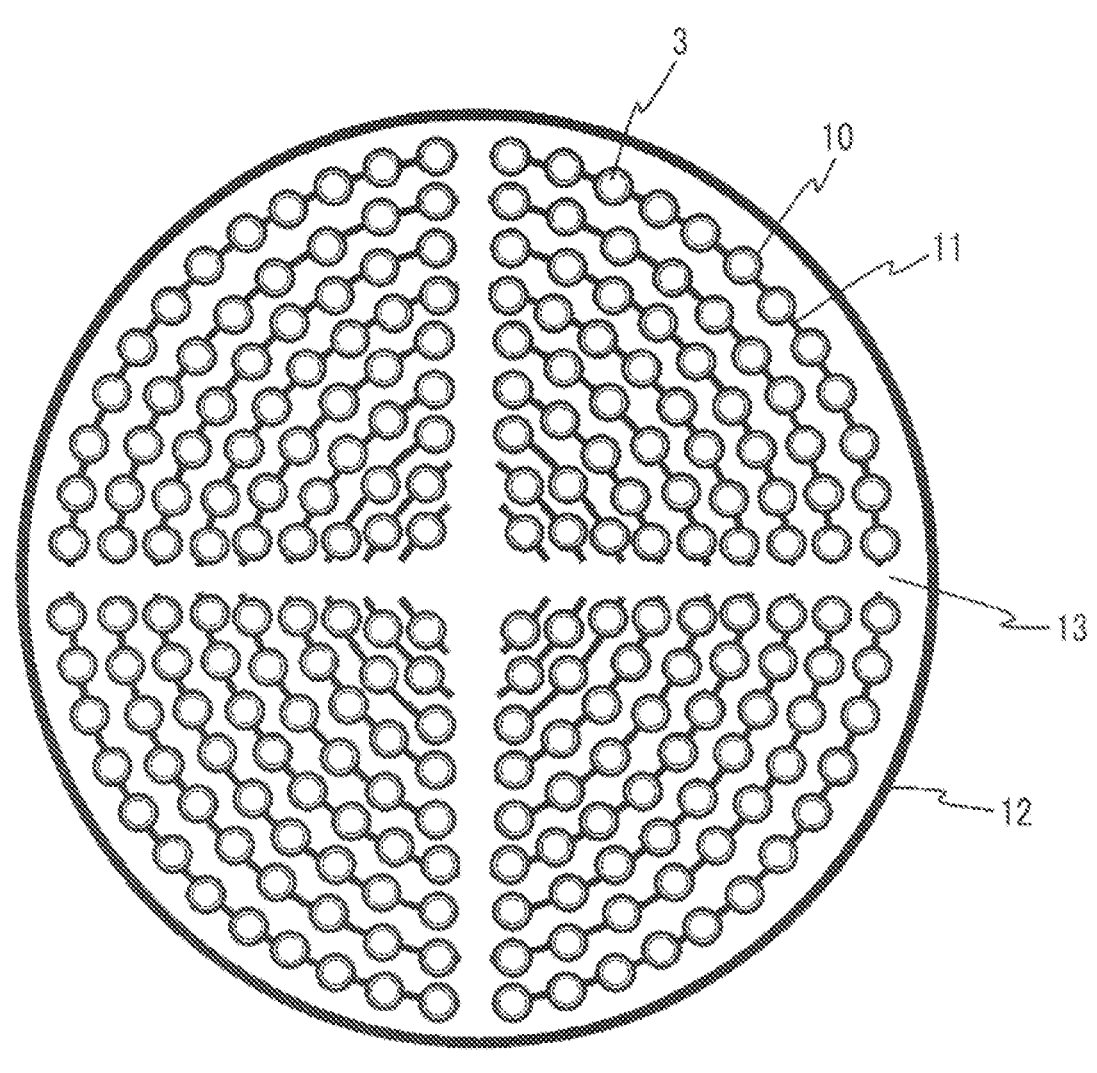
FIG. 8 is a cross-sectional view showing the reactor shown in FIG. 7.
Figure 9:
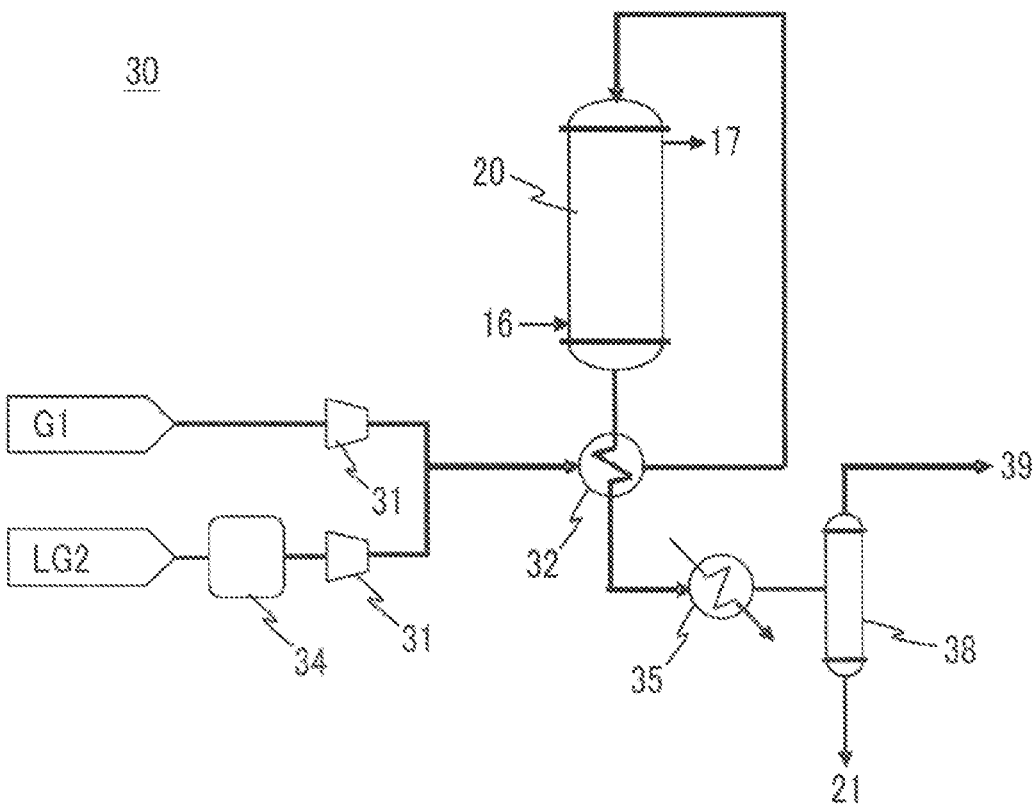
FIG. 9 is a diagram showing an example of a catalytic reaction device according to the present invention.

In yet still another aspect of the reaction tube according to the present invention, an end of the plate fin that is provided to protrude outward from the outer surface of the multilayer structure tube is connected to an outer surface of another adjacent multilayer structure tube. For example, as shown in FIG. 8, the plate fin 11 is provided such that the plate surface is parallel to the longitudinal direction of the multilayer structure tube (reaction tube 10), and an end of the plate fin 11 is connected to an outer surface of another adjacent multilayer structure tube (reaction tube 10). This makes it possible, for example, to suppress the vibration of the reaction tube, to control the flow of a heat transfer medium, and to promote the release of reaction heat. An aspect of the connection by the plate fin 11 is not particularly limited, and the reaction tubes may be connected in a concentric shape shown in FIG. 8, in a radial shape, or in a grid shape.

In a case in which the reaction tube 10 is adjacent to an inner surface of a heat transfer medium tube 12, the end of the plate fin, which is provided to protrude outward from the outer surface of the multilayer structure tube (reaction tube 10) may be connected to an inner surface of the heat transfer medium tube. Further, from the viewpoint of, for example, thermal expansion, it is preferable that the plate fin is made of the same material as the reaction tube.

The plate fin may be a plate-shaped fin without holes or a plate-shaped fin with holes. In the plate-shaped fin with holes, the holes can contribute to, for example, the control of the flow of the heat transfer medium, a reduction in dead space, and an increase in the contact area with the heat transfer medium. The hole is not limited to an elliptical hole and may have various shapes. In addition, the hole can be provided at an appropriate position according to the purpose. In addition, the plate fin may be made of a non-porous material or may be made of a porous material.

A catalytic reaction device or a gas phase catalytic reaction device according to the present invention includes a reactor including the reaction tube according to the present invention and a heat transfer medium tube.

It is preferable that one aspect of the reactor used in the present invention has a plurality of reaction tubes. It is preferable that each of the reaction tubes is disposed such that the longitudinal direction thereof is parallel to the longitudinal direction of the heat transfer medium tube. In addition, each of the reaction tubes may be connected to another adjacent reaction tube through the plate fin. All of the plurality of reaction tubes may be the reaction tubes according to the present invention, or some of the reaction tubes may be the reaction tubes according to the present invention. However, it is preferable that all of the reaction tubes are the reaction tubes according to the present invention.

The heat transfer medium tube 12 is a tube that has a heat transfer medium inlet 16 and a heat transfer medium outlet 17 and that has a heat transfer medium tube inner cavity 13 communicating from the heat transfer medium inlet to the heat transfer medium outlet. A surface that is cut at a right angle to the longitudinal direction of the heat transfer medium tube can have, for example, a circular shape, an egg shape, an elliptical shape, an oval shape, a rounded quadrangular shape, and a quadrangular shape. From the viewpoint of pressure resistance and weight reduction, it is preferable that the surface has a circular shape.

Then, the reactor used in the present invention has the following mechanisms: a mechanism in which a fluid raw material flows into the reaction tube inner cavity through the fluid inlet, the fluid raw material is brought into contact with the catalyst and chemically reacts with the catalyst in the reaction tube inner cavity, and a fluid mixture including a fluid product obtained by the chemical reaction flows out from the reaction tube inner cavity through the fluid outlet; a mechanism in which the heat transfer medium flows into the heat transfer medium tube inner cavity through the heat transfer medium inlet, and the heat transfer medium flows out from a first heat transfer medium tube inner cavity through the heat transfer medium outlet; and a mechanism in which the reaction tube is inserted into the heat transfer medium tube inner cavity, and the heat transfer medium in the heat transfer medium tube inner cavity exchanges heat with the fluid material in the reaction tube inner cavity through a reaction tube wall.

A fluid inlet 10a is separated from the heat transfer medium inlet 16 or the heat transfer medium outlet 17, and the fluid raw material flows into the reaction tube inner cavity through the fluid inlet. The separation between the fluid inlet and the heat transfer medium inlet or the heat transfer medium outlet can be performed, for example, by a plate 25 that holds a fluid-inlet-side end portion of the reaction tube.

Devices for preparing the fluid raw material, such as a mixing mechanism for mixing each component constituting the fluid raw material at a predetermined ratio and a tank for storing each component constituting the fluid raw material, a compressor 31, and a heat exchanger 32 can be installed on the upstream side of the reactor. In a case in which the raw material is a liquid such as liquefied carbon dioxide, a vaporizer 34 and the like can be provided for safe vaporization and the like. The components constituting the fluid raw material can be appropriately selected according to the chemical reaction performed in the reactor. For example, the fluid raw material used for a methanation reaction of carbon dioxide includes at least hydrogen gas and carbon dioxide gas. The amount of fluid raw material flowing into the reaction tube inner cavity can be appropriately set according to the chemical reaction performed in the reactor.

The heat transfer medium flows into the heat transfer medium tube inner cavity 13 through the heat transfer medium inlet. The heat transfer medium is not particularly limited as long as it does not deteriorate in a temperature range for performing a desired chemical reaction and can maintain fluidity. Specific examples of the heat transfer medium include: polyhydric alcohols such as glycerin and polyglycol; phenols and phenolic ethers such as anisole, diphenyl ether, and phenol; polyphenyls, such as terphenyl, and chlorinated benzenes and polyphenyls such as o-dichlorobenzene and polychloropolyphenyl; silicic acid esters such as tetraallyl silicate; naphthalene derivatives and fractionated tars and petroleum oils such as mineral oils; nitrates and nitrites (heat transfer salts) such as sodium nitrate, sodium nitrite, and potassium nitrate; silicones; fluorine compounds; glycols; and molten metals and alloys such as Na metal, K metal, Pb metal, Pb—Bi eutectic mixture, and Na—K alloy.

The pressure of the heat transfer medium flowing through the heat transfer medium tube inner cavity 13 and the pressure of the heat transfer medium flowing through the reaction tube inner cavity 3 are not particularly limited. It is preferable that the difference between the two pressures is less than the compressive strength of the non-porous layer in order to reduce the thickness of the non-porous layer from the viewpoint of heat transfer.

The disposition of the heat transfer medium inlet and the heat transfer medium outlet is not particularly limited. However, it is preferable to dispose the heat transfer medium inlet and the heat transfer medium outlet such that the heat transfer medium easily flows in a direction orthogonal to the longitudinal direction of the reaction tube. Partition plates are alternately provided from the left and right sides of the inner surface of the heat transfer medium tube such that the flow of the heat transfer medium can be meandered. In addition, the partition plates are provided in a spiral shape along the inner surface of the heat transfer medium tube such that the flow of the heat transfer medium can be swirled. Further, the partition plate may have a hole, through which the reaction tube can penetrate, so as to hold an intermediate portion of the reaction tube.

A fluid outlet 10_b_ is separated from the heat transfer medium inlet 16 or the heat transfer medium outlet 17, and a fluid mixture including a fluid product flows out from the reaction tube inner cavity 3 through the fluid outlet. The separation between the fluid outlet and the heat transfer medium inlet or the heat transfer medium outlet can be performed, for example, by a plate 26 that holds a fluid-outlet-side end portion of the reaction tube. The heat transfer medium flows out from the heat transfer medium tube inner cavity through the heat transfer medium outlet. It is possible to recycle the heat transfer medium flowing out from the heat transfer medium tube inner cavity.

In some cases, the fluid mixture flowing out through the fluid outlet includes, for example, an unreacted fluid raw material and a fluid by-product in addition to the fluid product. For example, the fluid product obtained by the methanation reaction of carbon dioxide is methane, and the fluid by-product is water.

The reaction tube 10 is inserted into the heat transfer medium tube inner cavity 13, and the heat transfer medium in the heat transfer medium tube inner cavity can exchange heat with the fluid in the reaction tube inner cavity 3 through the non-porous layer and the porous layer of the reaction tube. From the viewpoint of efficiency of heat exchange, it is preferable that the reaction tube has a plate-shaped porous layer which protrudes inward from the inner surface of the reaction tube wall. In addition, it is preferable that the reaction tube has a plate fin which protrudes outward from the outer surface of the reaction tube wall.

In general, in a tube-type reactor, a temperature distribution in a flow direction of the reaction tube is likely to be non-uniform. In some cases, a hot spot occurs in a chemical reaction that generates a large amount of heat. It is desired to suppress the occurrence of the hot spot and to uniformize the temperature distribution in the flow direction of the reaction tube.

The heat transfer medium inlet can be installed at a position close to a portion in which there is a concern that the hot spot will occur. Alternatively, the heat transfer medium tube inner cavity can be divided by partition plates, and the heat transfer medium inlet and the heat transfer medium outlet are provided in each of the divided parts such that the temperature of each of the heat transfer media flowing through the divided parts of the heat transfer medium tube inner cavity is relatively low on the side closer to the portion in which there is a concern that the hot spot will occur. In addition, the temperature distribution in the flow direction of the reaction tube can be uniformized by providing a large number of plate fins in the vicinity of the portion in which there is a concern that the hot spot will occur to increase the amount of heat transfer in the portion. The plate fin may be provided only in a portion which is close to the fluid inlet in the range in which the catalyst is placed, may be provided only in a portion which is close to the fluid outlet in the range in which the catalyst is placed, or may be provided over the entire range in which the catalyst is placed.

The catalytic reaction device or the gas phase catalytic reaction device according to the present invention is not particularly limited by a method for manufacturing the device. For example, the reaction tube, the heat transfer medium tube, and accessories can be prepared and assembled by welding, screwing, or the like to manufacture the catalytic reaction device or the gas phase catalytic reaction device.

The reaction tube, the heat transfer medium tube, the accessories, or the reactor having a complex shape can be manufactured by a method that includes laminating the cross-sectional shapes of them on the basis of 3D data of them to form a single three-dimensional object.

The 3D data may be 3D shape data of a target component. The 3D shape data can be designed by 3D CAD. The 3D data may be, for example, stereolithography (STL) data obtained by converting the 3D shape data. The STL data represents a three-dimensional shape as an aggregate of small triangles (polygons).

The formation (printing) of the three-dimensional object by laminating the cross-sectional shapes is performed by, for example, a powder bed fusion (PBF) method, a metal deposition method, a fused deposition modeling (FDM) method, a liquid metal inkjet method, a binder jet method, and a hybrid method that performs cutting during additive manufacturing by PBF. It is preferable to use the powder bed fusion (PBF) method or the metal deposition method among these methods.

The powder bed fusion method is a method that spreads a material powder and fuses and solidifies a portion to be printed with a laser or an electron beam as a heat source. Printing is performed by repeating the spreading of the material powder and the fusion and solidification. After the printing is ended, the powder that has not been solidified is removed, and a printed article is taken out.

Examples of the powder bed fusion method include a laser beam heat source method and an electron beam heat source method.

In a powder bed laser beam heat source method, additive manufacturing is performed by irradiating the spread material powder with a laser beam to fuse and solidify or sinter the spread material powder. In the laser beam heat source method, the fusion and solidification are generally performed in an inert atmosphere such as nitrogen. In the laser beam heat source method, positioning when the laser is emitted is performed by changing the angle of a mirror.

In the powder bed electron beam heat source method, the spread material powder is irradiated with an electron beam in a high vacuum to collide with the electron beam, and kinetic energy is converted into heat to fuse the powder. In the electron beam heat source method, fusion and solidification are generally performed in a vacuum. In the electron beam heat source method, the direction of the electron beam is changed by a lens using a magnetic field. As a result, the electron beam heat source method enables high-speed positioning.

The metal deposition method is a method in which printing is performed by laminating a fused metallic material in a predetermined place and solidifying the fused metallic material. The metal deposition method does not require the work of removing the powder after the printing is ended.

Examples of the metal deposition method include a laser beam heat source method that uses a metal powder as a material and an arc discharge method that uses an alloy wire as a material.

In the metal deposition laser beam heat source method, printing is performed by irradiating the metal powder with a laser beam at the same time as jetting the metal powder from a nozzle, supplying the metal powder to a molten pool, and solidifying the metal powder. A three-dimensional shape is drawn by moving a melting nozzle or a stage. A supply path of the metal powder can be switched to print dissimilar metals. Since a laser output is high, this method is suitable for high-speed printing.

In the metal deposition arc discharge method, printing is performed by fusing a metal wire by an arc discharge at the tip of the metal wire and laminating the metal wires. The metal deposition arc discharge method has relatively low device and material costs and enables high-speed printing.

After the printing, heat treatment can be performed for, for example, stress relief and strength increase. Conditions, such as temperature, time, and atmosphere, in the heat treatment can be appropriately set according to, for example, the metallic material to be used.

A specific aspect of a method for manufacturing a reaction tube according to the present invention includes: obtaining a multilayer structure tube that is composed of a tubular non-porous layer and a tubular porous layer laminated inside the tubular non-porous layer and that has a fluid inlet, a fluid outlet, and a reaction tube inner cavity communicating from the fluid inlet to the fluid outlet by repeatedly performing formation of a multilayer structure plate which is composed of an annular non-porous layer and an annular porous layer laminated inside the annular non-porous layer, the formation of the multilayer structure plate being performed by irradiating a spread material powder with a laser or an electron beam such that a portion corresponding to a non-porous layer is irradiated with a higher-energy laser or electron beam than a portion corresponding to a porous layer and by sintering the spread material powder; and supporting a catalyst on the porous layer. Metal powder, powder of an inorganic compound, such as an oxide, a carbide, a nitride, or a boride, or the like can be used as the material powder.

A method for obtaining a fluid product according to the present invention includes: supplying a fluid raw material into a reaction tube inner cavity through a fluid inlet in a catalytic reaction device according to the present invention; performing a chemical reaction while controlling a temperature of the fluid material in the reaction tube inner cavity by supplying a heat transfer medium into a heat transfer medium tube inner cavity through a heat transfer medium inlet, flowing the heat transfer medium through the heat transfer medium tube inner cavity, and discharging the heat transfer medium from the heat transfer medium tube inner cavity through a heat transfer medium outlet; and discharging a fluid mixture, which includes a fluid product obtained by the chemical reaction, from the reaction tube inner cavity through the fluid outlet.

In a method for producing carbon monoxide (CO), methanol, or methane, a carbon dioxide ($CO_2$) reduction reaction is performed using a gas including $CO_2$ and hydrogen ($H_2$) as a fluid raw material.

The amount of the gas containing $CO_2$ and $H_2$ to be introduced can be appropriately set according to, for example, the reaction speed and the capacity of the reaction tube inner cavity.

The $CO_2$ reduction reaction proceeds as follows according to the ratio of $CO_2$ and $H_2$.

$$CO_2+H_2 \rightarrow CO+H_2O$$

$$CO_2+3H_2 \rightarrow CH_3OH+H_2O$$

$$CO_2+4H_2 \rightarrow CH_4+2H_2O$$

A method for obtaining a catalytic reaction device and a fluid product according to the present invention can also be preferably used for, for example, a C1 chemical synthesis method other than the method for producing carbon monoxide (CO), methanol, or methane from the gas including carbon dioxide ($CO_2$) and hydrogen ($H_2$) Examples of the C1 chemical synthesis method include a method of producing carbon monoxide and hydrogen by the reaction of methane and water (steam), a method of producing carbon monoxide and hydrogen by the reaction of methane and carbon dioxide, a method of producing carbon dioxide and hydrogen by the reaction of carbon monoxide and water, a method of producing carbon dioxide and hydrogen by the reaction of methane and water, a method of producing methane and carbon dioxide by the reaction of carbon monoxide and hydrogen, a method of producing methanol by the reaction of carbon monoxide and hydrogen, a method of producing acetone and water by the reaction of carbon monoxide and hydrogen, and a method of producing carbon monoxide and hydrogen, ethylene and water, or methanol by the reaction of methane and oxygen.

In the present invention, it is possible to separate and purify the product (carbon monoxide (CO), methanol, or methane) obtained by the $CO_2$ reduction reaction and an unreacted substance (mainly $CO_2$). Examples of a separation and purification method include a membrane separation method, an adsorption separation method, an absorption separation method, a distillation separation method, and a cryogenic separation method. In the separation and purification of methane, the membrane separation method is preferable from the viewpoint of separation selectivity, a separation speed, and an inexpensive and compact facility. The unreacted substance (mainly $CO_2$) and low-concentration methane obtained in the separation and purification of methane can be used as the fluid raw material in the above-mentioned methane production method. Since carbon monoxide is toxic to the human body, it is preferable to perform treatment such that the concentration of carbon monoxide is equal to or less than 30 ppm. As a method of reducing the concentration of carbon monoxide, for example, the following methods can be used: a method of converting carbon monoxide into methane by the reaction of CO and methanation; a method of converting carbon monoxide into carbon dioxide by a CO selective oxidation reaction; and a method of adsorbing or absorbing carbon dioxide by, for example, an adsorbent or an absorbent.

Further, the methane obtained by the separation and purification can be supplied as fuel to a gas turbine. Power can be generated by this gas turbine.

Since a flue gas from the gas turbine usually includes carbon dioxide, it can be used as the fluid raw material in the above-mentioned methane production method.

The present invention can be used in various chemical reactions. The present invention is useful in the utilization of hydrogen produced by water electrolysis or the like, the utilization of carbon dioxide produced by the breathing of humans and animals or by the combustion of fuel or the like, the production of water, or the production of methane as fuel or the like. The present invention can also be used in, for example, a space station, a spacecraft, and a rocket.

The present invention can be provided with various chemical engineering devices, such as instruments, tubes, tanks, and towers, as long as they have the above-described characteristics. In addition, it is understood by those skilled in the art that modification, substitutions, additions, and omissions are included in the scope of the present invention as long as they do not depart from the gist of the present invention.

REFERENCE SIGNS LIST

1: Tubular porous layer
2: Tubular non-porous layer
3: Reaction tube inner cavity
4, 5, 6: Plate-shaped porous layer
10: Reaction tube
10a: Reaction tube fluid inlet
10b: Reaction tube fluid outlet
11: Plate fin
12: Heat transfer medium tube
16: heat transfer medium inlet
17: Heat transfer medium outlet
13: Heat transfer medium tube inner cavity
20: Reactor
9a: Reactor fluid inlet
9b: Reactor fluid outlet 25: Fluid-inlet-side holding plate
26: Fluid-outlet-side holding plate
30: Catalytic reaction device
31: Compressor
32: Heat exchanger
34: Vaporizer
35: Heat exchanger
38: Gas-liquid separator
21: Liquid outflow pipe
39: Gas outflow pipe

The invention claimed is:

1. A reaction tube comprising:
a multilayer structure tube that is composed of a tubular non-porous layer and a tubular porous layer laminated inside the tubular non-porous layer, has a fluid inlet, a fluid outlet, and a reaction tube inner cavity communicating from the fluid inlet to the fluid outlet, and has a distribution in a thickness of the porous layer in a range from the fluid inlet to the fluid outlet; and
a catalyst that is supported on the porous layer.

2. The reaction tube according to claim 1,
wherein the thickness of the porous layer is larger on a fluid outlet side than on a fluid inlet side or is larger on the fluid inlet side than on the fluid outlet side.

3. The reaction tube according to claim 1, wherein a sum of the thickness of the porous layer and a thickness of the non-porous layer is substantially constant in the range from the fluid inlet to the fluid outlet.

4. A reaction tube comprising:
two or more short reaction tubes,
wherein each of the short reaction tubes includes a multilayer structure tube that is composed of a tubular non-porous layer and a tubular porous layer laminated inside the tubular non-porous layer, has a fluid inlet, a fluid outlet, and a short reaction tube inner cavity communicating from the fluid inlet to the fluid outlet and a catalyst that is supported on the porous layer,
the fluid outlet of one short reaction tube is connected in series to the fluid inlet of another short reaction tube such that the short reaction tube inner cavities communicate with each other, and
a thickness of the porous layer of the one short reaction tube is substantially different from a thickness of the porous layer of another short reaction tube.

5. The reaction tube according to claim 1, further comprising:
a plate-shaped porous layer that is provided to protrude from an inner surface of the tubular porous layer toward the reaction tube inner cavity.

6. A catalytic reaction device comprising:
a reactor including the reaction tube according to claim 1 and a heat transfer medium tube that has a heat transfer medium inlet, a heat transfer medium outlet, and a heat transfer medium tube inner cavity communicating from the heat transfer medium inlet to the heat transfer medium outlet,
wherein the reactor has a mechanism in which a fluid raw material flows into the reaction tube inner cavity through the fluid inlet, the fluid raw material is brought into contact with the catalyst and chemically reacts with the catalyst in the reaction tube inner cavity, and a fluid mixture including a fluid product obtained by the chemical reaction flows out from the reaction tube inner cavity through the fluid outlet, a mechanism in which the heat transfer medium flows into the heat transfer medium tube inner cavity through the heat transfer medium inlet and the heat transfer medium flows out from a first heat transfer medium tube inner cavity through the heat transfer medium outlet, and a mechanism in which the reaction tube is inserted into the heat transfer medium tube inner cavity and the heat transfer medium in the heat transfer medium tube inner cavity exchanges heat with the fluid material in the reaction tube inner cavity through a reaction tube wall.

7. The catalytic reaction device according to claim 6, wherein there are a plurality of the reaction tubes each of which has a plate fin provided to protrude outward from an outer surface of the multilayer structure tube, and each of the reaction tubes is disposed parallel to a longitudinal direction of the heat transfer medium tube and is connected to another adjacent reaction tube through the plate fin.

8. A method for obtaining a fluid product, the method comprising:

supplying the fluid raw material into the reaction tube inner cavity through the fluid inlet in the catalytic reaction device according to claim 6;

performing a chemical reaction while controlling a temperature of the fluid material in the reaction tube inner cavity by supplying the heat transfer medium into the heat transfer medium tube inner cavity through the heat transfer medium inlet, flowing the heat transfer medium through the heat transfer medium tube inner cavity, and discharging the heat transfer medium from the heat transfer medium tube inner cavity through the heat transfer medium outlet; and discharging a fluid mixture including a fluid product obtained by the chemical reaction from the reaction tube inner cavity through the fluid outlet.

9. The method according to claim 8, wherein the fluid raw material includes hydrogen and carbon dioxide, and the fluid product includes carbon monoxide, methanol, or methane.

10. A method for manufacturing the reaction tube according to claim 1, the method comprising:

obtaining a multilayer structure tube that is composed of a tubular non-porous layer and a tubular porous layer laminated inside the tubular non-porous layer and has a fluid inlet, a fluid outlet, and a reaction tube inner cavity communicating from the fluid inlet to the fluid outlet by repeatedly performing formation of a multilayer structure plate which is composed of an annular non-porous layer and an annular porous layer laminated inside the annular non-porous layer, the formation of the multilayer structure plate being performed by irradiating a spread material powder with a laser or an electron beam such that a portion corresponding to a non-porous layer is irradiated with a higher-energy laser or electron beam than a portion corresponding to a porous layer and by sintering the spread material powder; and supporting a catalyst on the porous layer.

* * * * *